(12) United States Patent
Hüttermann et al.

(10) Patent No.: US 6,410,674 B2
(45) Date of Patent: *Jun. 25, 2002

(54) INTERMEDIATE PRODUCT FOR MANUFACTURING LIGAIN POLYMERS AND IT'S USE IN MANUFACTURING REAGENTS FOR MAKING COMPOSITE MATERIALS FROM PLANT FIBERS, WATERPROOF PAPERS AND CARDBOARDS, AND THERMOSETTING PLASTICS FROM DERIVATIVES

(75) Inventors: Aloys Hüttermann; Andrzej Majcherczyk; Carsten Mai, all of Göttingen; Annette Braun-Lüllemann, Bovenden; Merle Fastenrath; Sonja Noetzold, both of Göttingen, all of (DE)

(73) Assignee: Stockhausen GmbH & Co. KG, Krefeld (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,487

(22) PCT Filed: Jan. 19, 1998

(86) PCT No.: PCT/EP98/00254

§ 371 (c)(1),
(2), (4) Date: Feb. 4, 2000

(87) PCT Pub. No.: WO98/33848

PCT Pub. Date: Aug. 6, 1998

(30) Foreign Application Priority Data

Jan. 14, 1997 (DE) .......................................... 197 00 904
Jan. 14, 1997 (DE) .......................................... 197 00 906
Jan. 14, 1997 (DE) .......................................... 197 00 902

(51) Int. Cl.⁷ .............................................. C08L 97/00
(52) U.S. Cl. ........................ 527/403; 530/500; 530/502
(58) Field of Search ........................ 527/403; 530/500, 530/502

(56) References Cited

U.S. PATENT DOCUMENTS 4,432,921 A * 2/1984 Haars et al. ................ 264/109

OTHER PUBLICATIONS

Petrolite Corporation V. Watson, Comr. Patents (DC DC) 113 USPQ 248, Mar. 1957.*
Austenal Laboratories, Incorporated V. Nobilium Processing Company of Chicago et al. (DC N.ILL) 115 USP Q 44, Jun. 1957.*

* cited by examiner

*Primary Examiner*—Peter Szekely
(74) *Attorney, Agent, or Firm*—Proskauer Rose LLP

(57) ABSTRACT

The invention relates to an intermediate product for manufacturing polymers of lignin derivatives from the pulp industry, made by treating the lignin derivatives with phenol oxidizing enzymes in the presence of oxidation agents, characterized in that the lignin derivatives are (a) subjected to enzyme treatment for more than 3 hours in the presence of air, or (b) subjected to enzyme treatment for more than 10 minutes while air or oxygen is being passed through them, or (c) oxidized by treatment with chemical oxidation agents. The intermediate product is used in manufacturing polymers of lignin derivatives from the pulp industry, fiber-reinforced thermosetting composite materials from plant fibers, waterproof papers and cardboards, and thermosetting plastics from lignin derivatives.

10 Claims, 5 Drawing Sheets

INTERMEDIATE PRODUCT FOR MANUFACTURING LIGAIN POLYMERS AND IT'S USE IN MANUFACTURING REAGENTS FOR MAKING COMPOSITE MATERIALS FROM PLANT FIBERS, WATERPROOF PAPERS AND CARDBOARDS, AND THERMOSETTING PLASTICS FROM DERIVATIVES

The present application claims priority on German Patent Applications DE 197 00 902.6, DE 197 00 904.2, and DE 197 00 906.9, all dated Jan. 14, 1997.

BACKGROUND OF THE INVENTION

The present invention relates to an intermediate product for manufacturing polymers from lignin derivatives which are by-products of the pulp industry, and to the use of these intermediate products in manufacturing highly reactive reagents for making composite materials from plant fibers, waterproof paper and cardboards, and thermosetting plastics from lignin derivatives.

DE 37 992 C2 describes a method for manufacturing a binding agent for wood products, using phenolic substances, in particular lignin sulfonate, whereby enzymes are added to the phenolic substance to activate same, the phenols polymerize according to a radical mechanism, while the phenolic substance is converted into an active binding agent. It is known that this reaction takes place in the presence of oxygen, such as atmospheric oxygen, but until now, such an activated binding agent has not been caused to react with oxygen for a long period of time or by intensive aeration.

SUMMARY OF THE INVENTION

Surprisingly it was found that lignin derivatives from the pulp industry, such as kraft lignin or lignin sulfonate, with phenol oxidizing enzymes such as phenol oxidase or laccase, form a particularly reactive lignin product as an intermediate product when caused to react for a long period of time or intensively with oxygen, air or other chemical oxidizing agents. This intermediate product can be isolated and stored for a long time, and it further reacts with other non-activated lignin derivatives to form a polymer of high molecular weight. The intermediate product can be characterized in that the material is caused to react with laccase. After that reaction, it shows a typical ESR spectrum with a signal for phenoxyradicals in the range of about 3400 gauss, which, however, does not remain constant as a typical radical signal. However, surprisingly, the increased reactivity of the intermediate product remains intact even after long periods of time, for example for months. This means that this activated intermediate product is considerably more active when caused to react with phenol oxidizing enzymes than non-treated lignin derivatives, and that the typical ESR spectrum is therefore formed at a considerably higher intensity than lignin derivatives not treated in that manner.

The intensity of the signal of the activated intermediate product is at least five times that of the signal of the lignin derivative serving as the initial product. For example, the signal is measured under the following conditions: 77° K.; 9.5 GHz; ESR attenuation 20 dB; mod. frequ. 100 MHz, mod. amplitude 4.0 gauss.

The activated intermediate product can be obtained when technical lignins such as lignin sulfonates, kraft lignin, organosolve lignin, acetosolve lignin, ASAM lignin, etc., which are pulp industry by-products, are treated for a long time with air or oxygen in the presence of phenol oxidizing enzymes. Even after a period of about three hours, for example, but especially after 15 or 20 hours, the phenoxyradical signal can be found to increase. When air or oxygen are passed through under pressure, the increased signal occurs after a significantly shorter period of time, namely after 10 minutes or, as an example, after about 30 minutes.

The intermediate product can also be obtained with chemical oxidizing agents. For example, potassium permanganate, bichromate or ozone, which are customary agents in lignin chemistry, can serve that purpose.

The enzymatic formation of the activated intermediate product is possible only when large amounts of oxygen are present. Since at room temperature, oxygen dissolves in water only at the rate of 9 mg/L, the formation of the intermediate product is encouraged only when more oxygen is added, either through aeration or in the form of oxidation agents. Even when it takes a long time for the oxygen equilibrium to be established, enough oxygen may have acted upon the lignin derivative after some time.

In the presence of phenol oxidizing enzymes, the activated intermediate product reacts with non-activated lignin derivatives that may be obtained, for example, in pulp production. This is accompanied by the formation of polymeric lignin products, whereby the molecular weights are considerably higher than those obtained when phenol oxidizing enzymes act upon lignin derivatives without the presence of activated lignin derivatives. They are generally at least twice as high.

The lignin polymers obtained in the polymerization of lignin derivatives in the presence of active intermediate products can be used for making highly active reagents for the manufacture of composite materials from plant fibers, waterproof papers and cardboards, and thermosetting plastics from lignin derivatives. It is thus possible for the first time to produce fiber-reinforced thermosetting plastics from renewable raw materials completely by in situ polymerization.

DETAILED DESCRIPTION OF THE INVENTION

Figure 1:
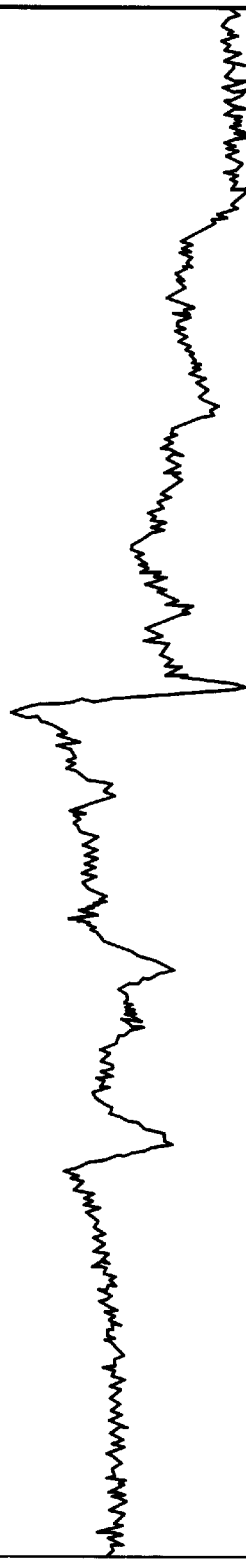
FIG. 1 shows an ESR spectrum of 1% lignin sulfonate in accordance with an embodiment of the present invention.
Figure 2:
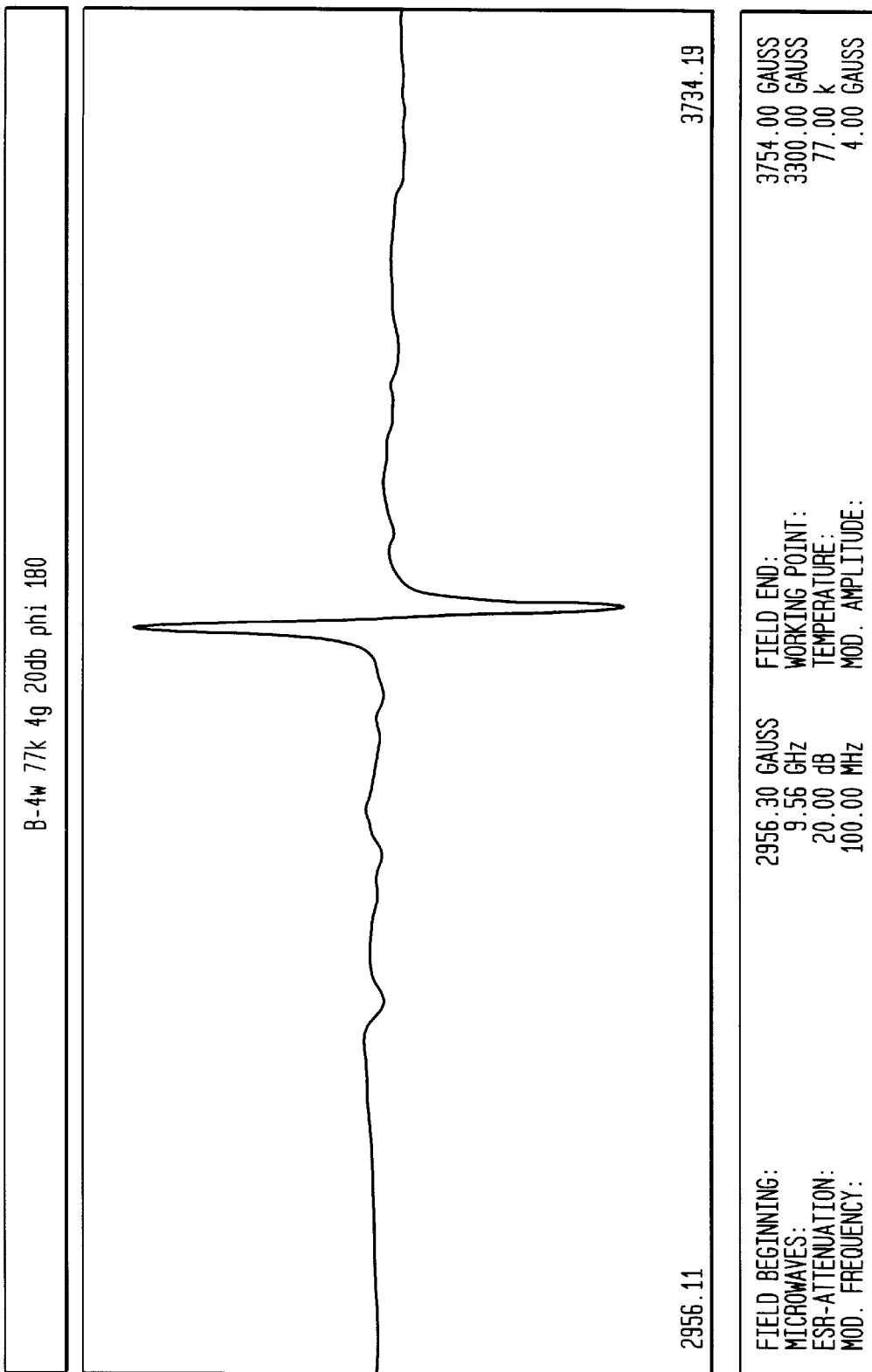
FIG. 2 shows an ESR spectrum of lignin sulfonate in accordance with an embodiment of the present invention.

In comparison with the lignin used as the initial material, the activated lignin has an ESR spectrum in which the phenoxyradical signal is of considerably higher intensity. This is demonstrated by FIGS. 1 and 2. FIG. 1 shows an ESR spectrum of 1% lignin sulfonate with an addition of laccase (4 U/ml) after 30 minutes of incubation without, oxygen treatment. FIG. 2 shows the corresponding spectrum of lignin sulfonate which was incubated with laccase for 20 hours under increased oxygenation and then autoclaved and stored for three months. Following renewed incubation with laccase (4 U/ml, 30 min. incubation without oxygen treatment), a comparison between the strongest signal at about 3400 gauss and the background signals shows that the intensity of the phenoxyradical signal was at least five times as strong as in FIG. 1.

So high is the reactivity of the resulting intermediate product that even lignin sulfonate, a polymer of extremely high water solubility, forms a water-insoluble product.

The invention is described below by means of the examples:

EXAMPLE 1

We dissolved 20 g of lignin sulfonate in 80 ml of McIlvaine buffer, pH 5.5, and added 800 U/ml laccase. We shook the solution for 20 hours In a 500 ml erlenmayer flask at 37° C. in a water bath. Then we autoclaved the solution. We stored the resulting lignin sulfonate for two months. Following renewed incubation with laccase (4 U/ml, 30 min. incubation without oxygen treatment), the ESR spectrum was as in FIG. 2.

EXAMPLE 2

To activated lignin sulfonate according to Example 1, we added kraft lignin at the ratio of 1:10 and suspended with a concentration of 100 mg/10 ml in buffer, and incubated for 6 hours with laccase (500 U/ml) in a sealed test tube, without special oxygen treatment. Simultaneously, we carried out corresponding control tests with non-activated lignin and incubated without laccase. Then we isolated the resulting lignins and measured the molecular weight distribution in the HPLC.

The following molecular weights were determined:

| | |
|---|---|
| non-activated kraft lignin | 5,400 g/mol |
| non-activated kraft lignin incubated with laccase | 6,300 g/mol |
| non-activated kraft lignin plus activated lignin without laccase | 6,000 g/mol |
| non-activated kraft lignin plus activated lignin incubated with laccase | 11,000 g/mol |

EXAMPLE 3

We adjusted a lignin suspension consisting of
80 ml of McIlvain buffer, pH 4.5
16.5 g of kraft lignin
4 g lignin sulfonate
with concentrated laccase to a final concentration of 800 U/ml, aerated with compressed air for 3 hours and stirred. We applied the solution thus obtained to a cotton fabric commonly used in the manufacture of thermoplastic composite materials of renewable raw materials, and air-dried it. Our subsequent examination of the product showed a 42% degree of adhesion (absolutely dry lignin in relation to absolutely dry fiber).

To determine the bonding rate of the applied lignin, we incubated the coated fabric for three hours in water or in 0.1 m of NaOH and subsequently determined the volume of dissolved lignin. After water treatment, 2% (w/w) and after alkali treatment, 30% (w/w) of the applied lignin peeled off the cotton fiber again.

EXAMPLE 4

In a high vacuum, we sprinkled gold onto cotton fiber coated according to the method described in Example 3 and examined it under a scanning electron microscope.

Figure 3:
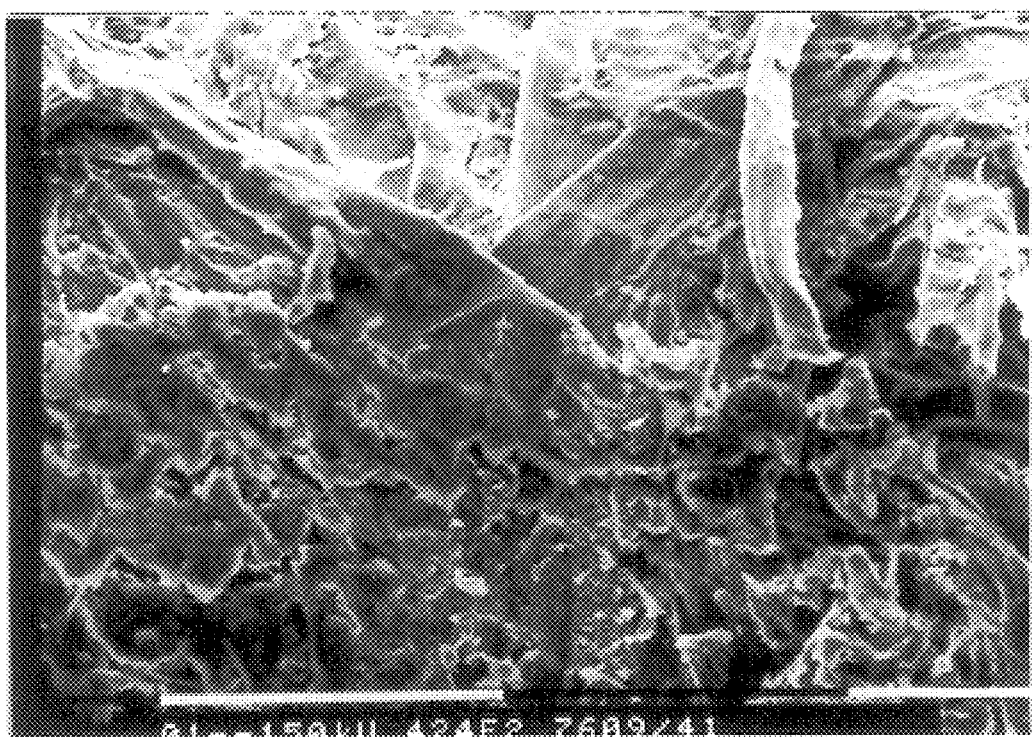
FIGS. 3 through 6 show the bond between coating and fiber in accordance with embodiments the present invention.
Figure 4:
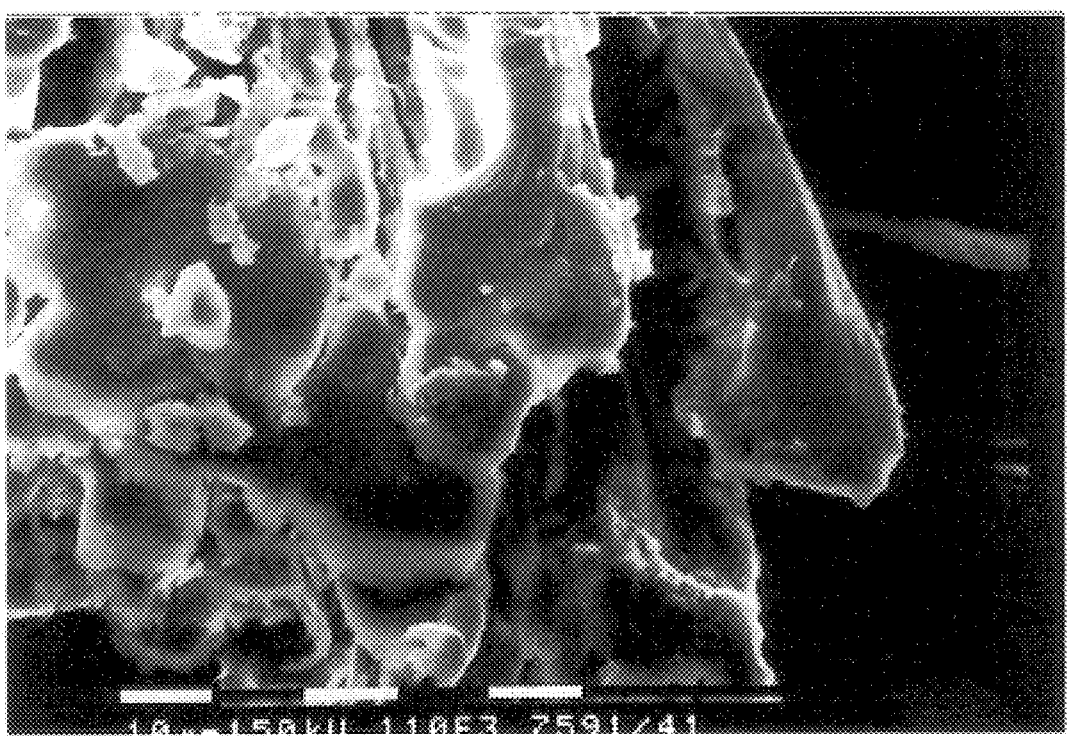
Figure 5:
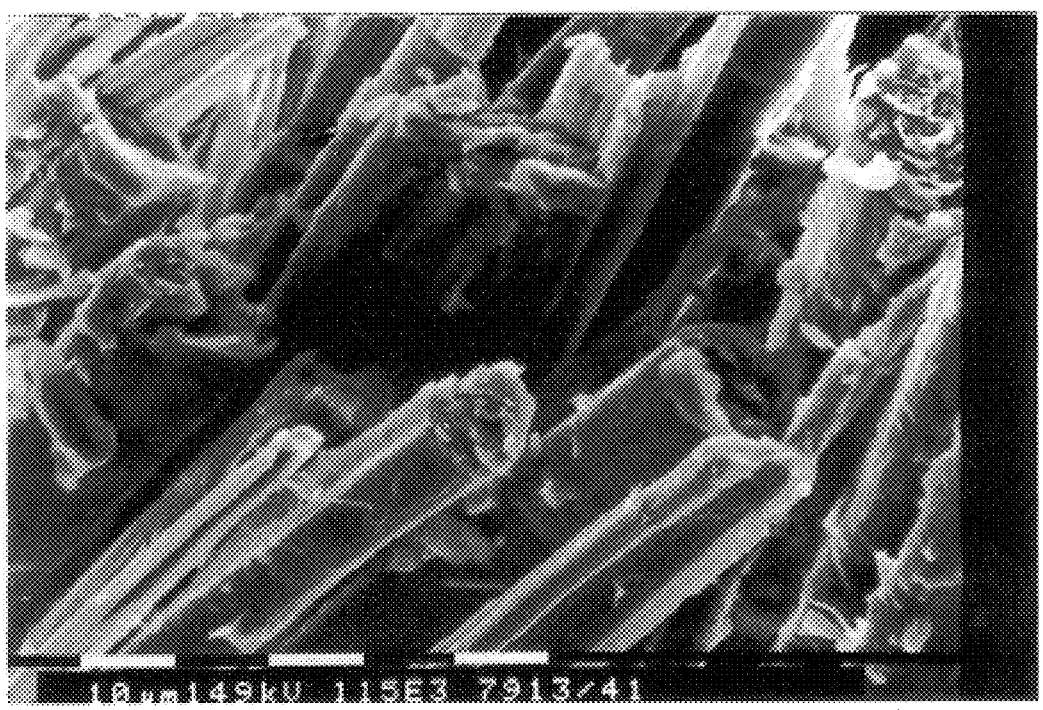

FIGS. 3, 4 and 5 show that an intimate bond can be recognized between the coating and the fiber without a transitional zone being visible. This shows that the coating is caused by a true covalent bond between the lignin and the fiber surface.

EXAMPLE 5

We adjusted 20% lignin glue consisting of
80 ml of McIlvain buffer, pH 4.5
16.5 g of kraft lignin
5 g of lignin sulfonate
with concentrated laccase to a final concentration of 800 U/ml, aerated with compressed air for 3 hours and stirred. After 3 hours, we diluted the solution thus obtained with a laccase solution (800 U/ml in buffer, pH 4.5) at a ratio of 1 ±4 and applied it to both sides of a filter paper.

We air-dried the treated papers overnight. The papers had a coating ratio of 9% weight-by-weight lignin to weight-by-weight paper.

We then measured the resistance of the coating to water and 0.1 M NaOH and determined the water absorption rate.

A three-hour incubation in water caused 3% of the applied amount of lignin to peel off; incubation for the same period in 0.1 N³ NaOH caused 31% of the lignin to peel off the paper surface.

In comparison with the uncoated controls, the coated papers had a water absorption rate that was 30% lower. Water tear resistance was clearly improved: while the untreated paper dissolved into individual fibers, the coated paper was still completely intact.

EXAMPLE 6

In a high vacuum, we sprinkled gold onto paper coated according to the method described in Example 3 and examined it under a scanning electron microscope.

Figure 6:
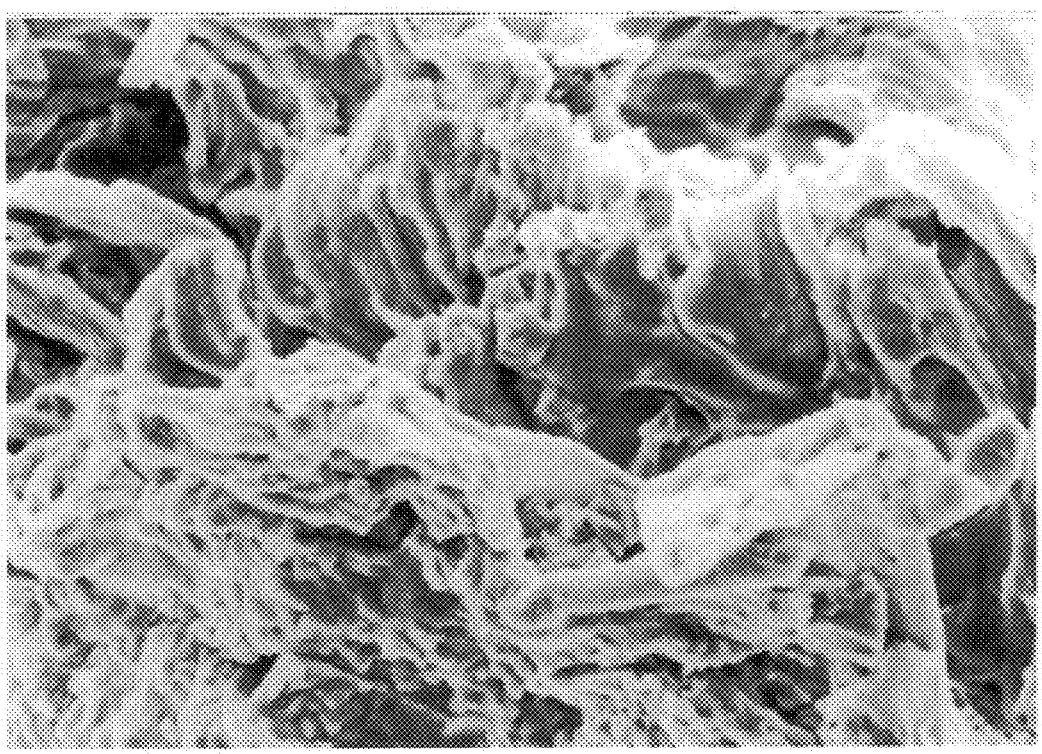

FIG. 6 shows that an intimate bond can be recognized between the coating and the paper fiber without a transitional zone being visible. This shows that the coating is caused by a true covalent bond between the lignin and the fiber.

EXAMPLE 7

Figure 7:
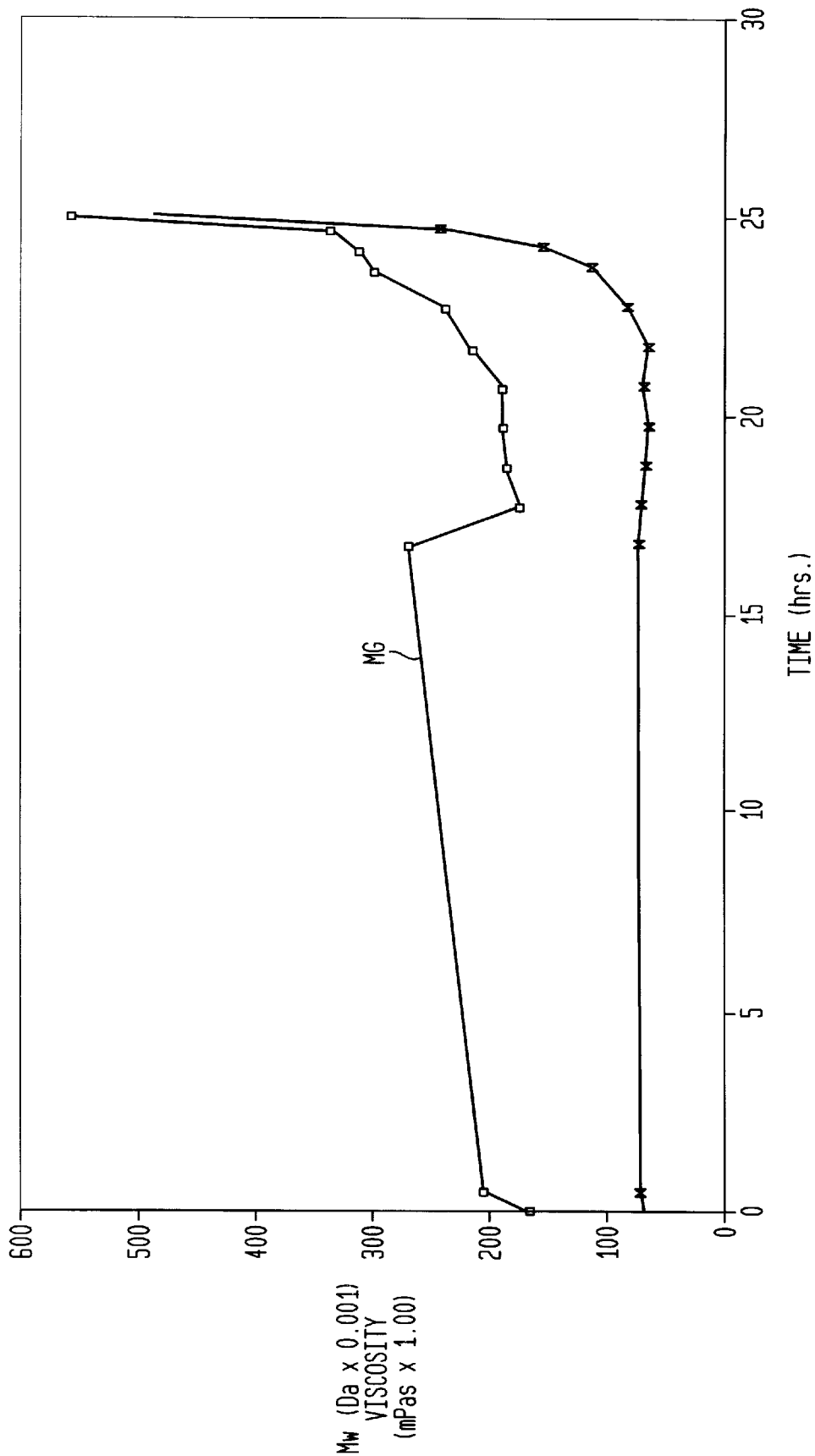
FIG. 7. shows a graph of the molecular weight and viscosity of a solution in accordance with an embodiment of the present invention.

We adjusted a solution consisting of 80 ml of McIlvain buffer, pH 4.5, and 16.5 of lignin sulfonate with concentrated laccase to a final concentration of 800 U/ml, and shook it for 25 hours at 37° C. in a water bath. During the last few hours, the molecular weight (measured in the HPLC) as well as the viscosity of the solution increased sharply (FIG. 7). The product thus obtained was insoluble in water, 0.1 m NaOH and in the customary organic solvents such as ethanol, ether, acetone or ethyl acetate.

What is claimed is:

1. Method for manufacturing polymers of lignin-based compounds from the pulp industry by treating the lignin-based compounds with phenol oxidizing enzymes in the presence of oxidation agents, characterized in that the lignin-based compounds are:

(a) subjected to enzyme treatment for more than 3 hours in the presence of air, or (b) subjected to enzyme treatment for more than 10 minutes while air or oxygen is being passed through them, or (c) oxidized by treatment with chemical oxidation agents, and that the activated intermediate product thus obtained is caused to react with non-activated lignin-based compounds while polymeric lignin products are formed.

2. Method according to claim 1, wherein the lignin-based compounds are selected from the group consisting of kraft lignin, lignin sulfonate, organosolve lignin, and ASAM lignin.

3. Method according to claim 1, wherein the phenol oxidizing enzymes are selected from the group consisting of phenol oxidase and laccase.

4. Method according to claim 1, characterized in that the enzyme treatment according to step (a) is performed for more than 15 hours.

5. Method according to claim 1, characterized in that the enzyme treatment according to step (b) is performed for more than 30 minutes.

6. Method according to claim 1, characterized in that the activated intermediate product or its solution is isolated.

7. Polymers of lignin-based compounds from the pulp industry manufactured according to the method of claim 1.

8. Fiber-reinforced thermosetting composite materials of plant fibers made with the activated intermediate product of claim 1.

9. Waterproof papers and cardboards made with the activated intermediate product of claim 1.

10. Thermosetting plastics made with the activated intermediate product of claim 1.

\* \* \* \* \*